US012594329B2

(12) United States Patent
van Engelenburg

(10) Patent No.: US 12,594,329 B2
(45) Date of Patent: Apr. 7, 2026

(54) VIRUS-LIKE PARTICLES

(71) Applicant: University of Denver, Denver, CO (US)

(72) Inventor: Schuyler B. van Engelenburg, Denver, CO (US)

(73) Assignee: University of Denver, Denver, CO (US)

( * ) Notice: Subject to any disclaimer, the term of this patent is extended or adjusted under 35 U.S.C. 154(b) by 1129 days.

(21) Appl. No.: 17/522,150

(22) Filed: Nov. 9, 2021

(65) Prior Publication Data

US 2022/0143173 A1 May 12, 2022

Related U.S. Application Data

(60) Provisional application No. 63/111,455, filed on Nov. 9, 2020.

(51) Int. Cl.

| | |
|---|---|
| *A61K 39/215* | (2006.01) |
| *A61P 37/04* | (2006.01) |
| *C07K 14/005* | (2006.01) |
| *C07K 14/165* | (2006.01) |
| *C12N 7/00* | (2006.01) |
| *C12N 15/86* | (2006.01) |
| *G01N 33/569* | (2006.01) |
| *A61K 39/00* | (2006.01) |

(52) U.S. Cl.
CPC .......... *A61K 39/215* (2013.01); *C07K 14/005* (2013.01); *C12N 7/00* (2013.01); *G01N 33/56983* (2013.01); *A61K 2039/5254* (2013.01); *A61K 2039/5258* (2013.01); *C07K 2319/00* (2013.01); *C12N 2770/20022* (2013.01); *C12N 2770/20023* (2013.01); *C12N 2770/20034* (2013.01); *C12N 2770/20051* (2013.01); *G01N 2333/165* (2013.01)

(58) Field of Classification Search
CPC C07K 14/005; C07K 14/165; C07K 2319/00; C07K 14/08; C12N 2770/20023
See application file for complete search history.

(56) References Cited

PUBLICATIONS

Tregoning et al., "Vaccines for Covid-19", Clinical & Experimental Immunology, 2020, 202:162-192.*
Fernandes et al., "Reporter replicons for antiviral drug discovery against postive single-stranded RNA viruses", Viruses, 2020, 12:1-22.*
Moon et al., "Construction of SARS-CoV-2 Virus-like Particles in Plant", Scientific Reports, vol. 12, No. 1005, 7 pages, 2022.
Prates-Syed et al., "VLP-Based COVID-19 Vaccines: An Adaptable Technology Against the Threat of New Variants", Vaccines, vol. 9, No. 1409, 17 pages, 2021.
Xu et al., "Construction of SARS-CoV-2 Virus-Like Particles by Mammalian Expression System", Frontiers in Bioengineering and Biotechnology, vol. 8, No. 862, 6 pages, Jul. 2020.

* cited by examiner

*Primary Examiner* — Barry A Chestnut

(74) *Attorney, Agent, or Firm* — NOD Law PC

(57) ABSTRACT

Virus-like particles, compositions and antibody detection tests with virus-like particles, and a method of producing virus-like particles are disclosed. The method includes generating a modified viral genome based on a viral genome, wherein a portion of the viral genome is removed to generate the modified viral genome configured to yield virus-like particles that are unable to replicate, and producing one or more virus-like particles using the modified viral genome.

9 Claims, 9 Drawing Sheets

VIRUS-LIKE PARTICLES

CLAIM OF PRIORITY UNDER 35 U.S.C. § 119

The present application for patent claims priority to Provisional Application No. 63/111,455 entitled "SYSTEMS AND METHODS FOR GENERATING VIRUS-LIKE PARTICLES" filed Nov. 9, 2020, and assigned to the assignee hereof and hereby expressly incorporated by reference herein.

BACKGROUND

Field

The present disclosed embodiments relate generally to virology and immunology, and more specifically to systems and methods for generating virus-like particles.

Background

To date, the SARS-CoV-2 pandemic has killed millions of people worldwide. Various vaccine approaches have been pursued, however, efforts in this direction are unnecessarily narrow in scope. Several vaccine approaches are redundant, focusing on efforts to educate the immune system on a single subdomain, the entire ectodomain, or through genetic expression of the open-reading frame of the SARS-CoV-2 Spike envelope glycoprotein (S). Coronaviruses, however, utilize additional structural proteins Membrane (M) and Envelope (E) to build a protective membrane around the nucleoprotein (N) and large RNA genome. Further, for the related SARS-CoV-1, the accessory factors Orf3a and Orf7b are incorporated into the viral envelope and have been suggested to be structural proteins. Aside from S, these ectodomain epitopes, while not directly mediating virus entry into naïve cells, are presented to the human immune system during viral infection. Furthermore, both SARS-CoV-1 and SARS-CoV-2 each have been shown to elicit a polyclonal response to many of the structural antigens as assessed by convalescing patient serum. It is therefore necessary to develop novel holistic immunogens that incorporate the gamut of antigens displayed by SARS-CoV-2.

A converse approach to vaccine development is the production of fully infectious virus followed by subsequent attenuation with inactivating chemicals or serial passage in animal or tissue cultures. These vaccine approaches benefit from eliciting a broad immune response to all antigens of the virus; however, these approaches carry risk of eliciting a skewed immune response and inflammatory pathology. Specifically, chemical inactivation of fully infectious SARS-CoV-2 has been shown to change the structure of the major Spike protein, leading to the presentation of non-native antigens that drive antibody responses away from critical neutralizing sites on the virus. A vaccine approach that preserves the benefits of inactivated whole virus, namely eliciting a potent polyclonal response to all native structural antigens, yet possessing the necessary safety, modularity, and scalability of targeted subunit vaccines, is desperately needed.

SUMMARY

The following presents a simplified summary relating to one or more aspects and/or embodiments disclosed herein. As such, the following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Some aspects of the present disclosure may be characterized as a method for producing replication-incompetent virus-like particles. The method may include generating a modified viral genome based on a viral genome, wherein a portion of the viral genome is removed to generate the modified viral genome configured to yield virus-like particles that are unable to replicate. The method may also include producing one or more virus-like particles using the modified viral genome.

Other aspects of the present disclosure may be characterized as an antibody detection test including one or more virus-like particles that are unable to replicate and comprise a plurality of envelope antigens of a virus in a native configuration. The antibody detection test may also include means for exposing the one or more virus-like particles to one or more antibodies associated with the virus.

Other aspects of the present disclosure may be characterized as a composition including one or more virus-like particles that are morphologically and biochemically similar to a virus and are unable to replicate, wherein the virus-like particles are associated with a modified viral genome having a genome of the virus with a removed portion.

BRIEF DESCRIPTION OF THE DRAWINGS

FIGS. 2A and 2B illustrate an exemplary embodiment of a minimal replicase SARS-CoV-2 virus-like particle system, in accordance with one or more embodiments described herein, wherein FIG. 2A illustrates an exemplary segmented reverse genetics system of the minimal replicase SARS-CoV-2 virus-like particle system, and FIG. 2B illustrates an exemplary production of sub-genomic RNA transcripts and viral structural and accessory proteins in a transfected cell expressing the minimal replicase SARS-CoV-2 virus-like particle system;

FIGS. 2C and 2D illustrate an exemplary embodiment of a two-plasmid minimal replicase SARS-CoV-2 virus-like particle system, in accordance with one or more embodiments described herein, wherein FIG. 2C illustrates an exemplary pReplicase plasmid, and FIG. 2D illustrates an exemplary pStructural plasmid;

FIGS. 4A-D illustrate a biochemical analysis of an exemplary embodiment of a minimal replicase SARS-CoV-2 virus-like particle system, in accordance with one or more embodiments described herein, wherein FIG. 4A illustrates an exemplary western blot time-course analysis of a minimal replicase polypeptide proteolytic processing by Nsp5, FIG. 4B illustrates exemplary results of a RT-PCR amplification of SARS-CoV-2 sub-genomic RNA from purified poly-A containing message from cells transfected with a minimal replicase SARS-CoV-2 reverse genetics system (+) or mock transfected (−), FIG. 4C illustrates an exemplary anti-N and anti-S western blot as well as an exemplary anti-M western blot, both of transfected Vero cells, and FIG. 4D illustrates exemplary anti-S, anti-N, and anti-M western blots of virus-like particles produced from said transfected Vero cells.

DETAILED DESCRIPTION

Figure 1:
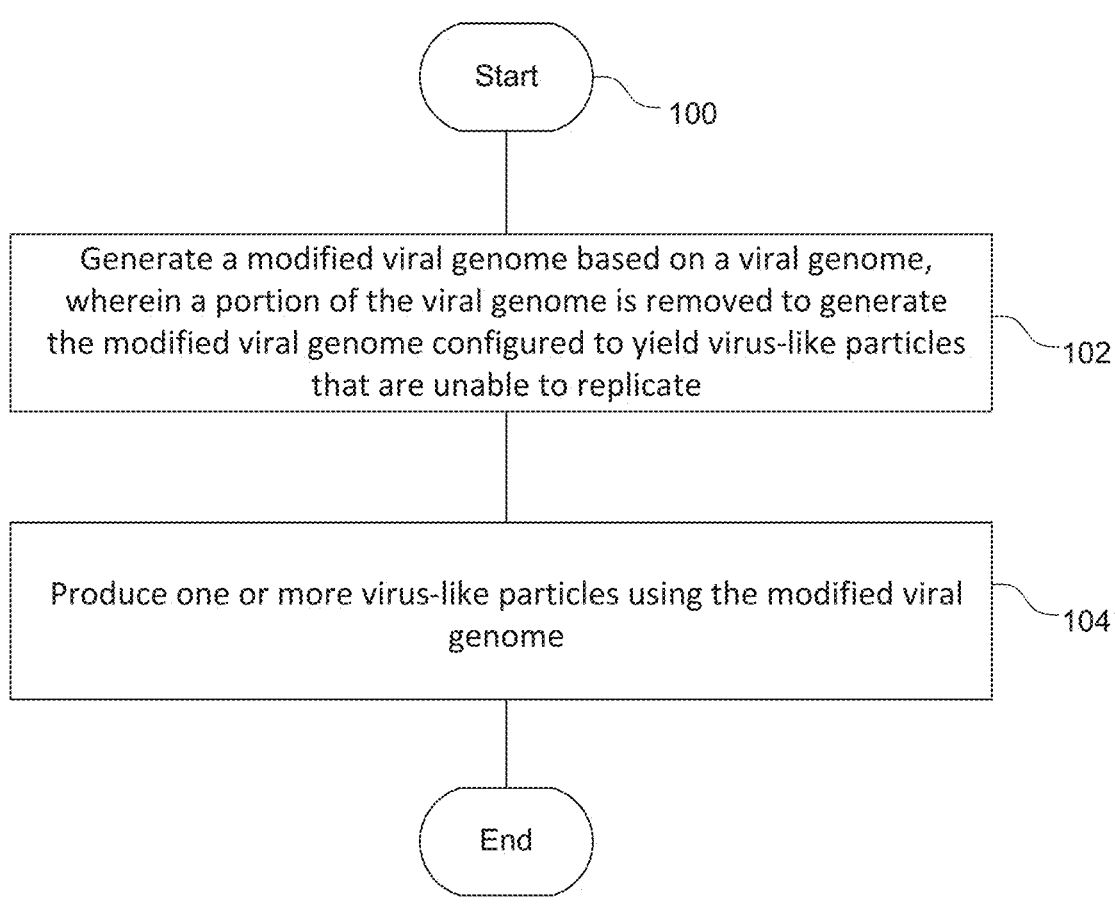
FIG. 1 illustrates a flowchart depicting an exemplary method for producing virus-like particles in accordance with one or more embodiments described herein.

The word "exemplary" is used herein to mean "serving as an example, instance, or illustration." Any embodiment described herein as "exemplary" is not necessarily to be construed as preferred or advantageous over other embodiments.

The present disclosure may enable design and production of non-infectious virus-like particles (VLPs), such as SARS-CoV-2 VLPs, which may be replication-incompetent VLPs with a native configuration of envelope antigens, such as Spike envelope glycoproteins (S). The present disclosure may also enable these VLPs to be used in vaccination or diagnostic detection of antibodies from infected individuals. These VLPs may possess high-density display of all putative envelope antigens and the core nucleoprotein, all of which have been shown to some extent to be targeted by antibodies from patients infected by SARS-CoV-2 and, similarly, by antibodies from patients infected by the related SARS-CoV-1. The present disclosure may enable a SARS-CoV-2 VLP vaccine approach that may preserve the native structure and stoichiometry of surface antigens but is unable to replicate and cause unnecessary inflammatory responses. This approach may potentially be impactful as a vaccine candidate because such VLPs may be safe to produce in large quantities and upon administration, the engineered VLP system may educate the human immune system toward both structural and accessory antigens, thus bolstering a broad polyclonal immune response to challenge with community acquired SARS-CoV-2 infections. Furthermore, the present disclosure may enable rapid prototyping of new immunogens through facile reverse genetic manipulations to understand important VLP determinants that may elicit a potent immune response while minimizing skewed inflammatory responses relative to chemical inactivation of fully infectious particles. Additionally, the present disclosure may enable prevalent immune escape mutants of emergent SARS-CoV-2 strains to be rapidly generated under biosafety level 2 (BSL-2) conditions and tested for safety and immunological protection. The ability to use BSL-2 conditions to generate VLPs, rather than BSL-3, may enable faster, safer, and more cost-efficient scale-up production in manufacturing. By implementing the teachings of the present disclosure, significant improvements in virus understanding, detection, and treatment may be obtained, potentially improving vaccination efficacy and diagnostic detection of antibodies from infected individuals.

In some embodiments, the present disclosure may comprise an optimized genetic system, such as a reverse genetics system, to program the SARS-CoV-2 genome to generate a minimal replicase SARS-CoV-2 virus-like particle system and create SARS-CoV-2 VLPs. The optimized genetic system may utilize one or more non-obvious alterations to the genome in the creation of VLPs.

One aspect of the present disclosure relates to the cloning of two segments of a SARS-CoV-2 genome (roughly each <⅓ of the genome) into deoxyribonucleic acid form (DNA; virus genome is a ribonucleic acid or RNA virus). Segmentation and removal of ⅓ of the genome may provide safety and render the virus unable to replicate. The majority of the orf1a genes may be dispensable for the generation of VLPs. A modular system of two DNA plasmids, referred to as pStructural and pReplicase, may be generated.

Another aspect of the present disclosure relates to the engineering of transcriptional switching elements and their spacing in a pStructural cassette, which may be adjusted to enable improved VLP production. For example, a pStructural plasmid may comprise encoded messenger RNA transcripts able to produce specific polypeptides, for the following open-reading frames (ORFs) for S, 3a-b, E, M, 6, 7a-b, 8, 9b-c, and N; transcriptional template switching may produce subgenomic RNA relating to each transcript, and the respective proteins may be produced in a precise stoichiometry to enable VLP assembly.

Another aspect of the present disclosure relates to the self-cleaving (scarless) expression of RNA to mimic the native ends of a SARS-CoV-2 RNA genome for replication, which may comprise liberating an RNA mimic of the viral genome after RNA polymerase II-mediated transcription, such as in the generation of pStructural, enabling the removal of non-viral genetic material upon completion of RNA polymerase II transcription. For example, self-cleaving RNA elements, such as hammerhead ribozyme (HHr) and Hepatitis Delta Virus ribozyme (HDVr), may be incorporated to provide such self-cleaving functionality.

Figure 2A:
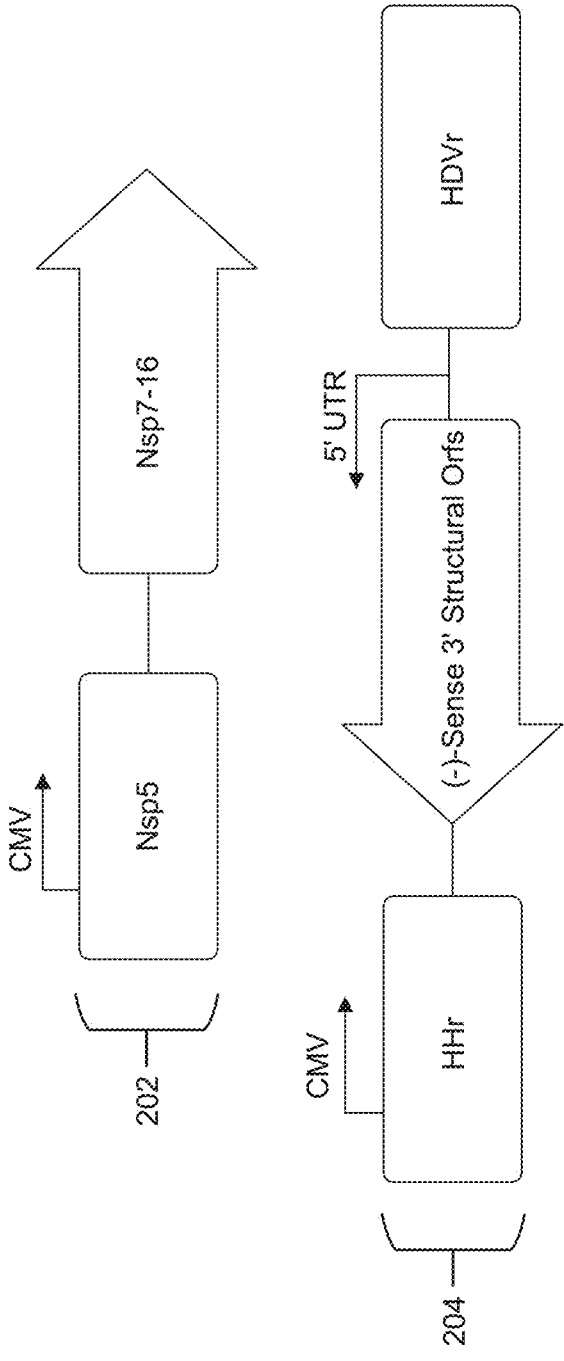
Figure 2B:
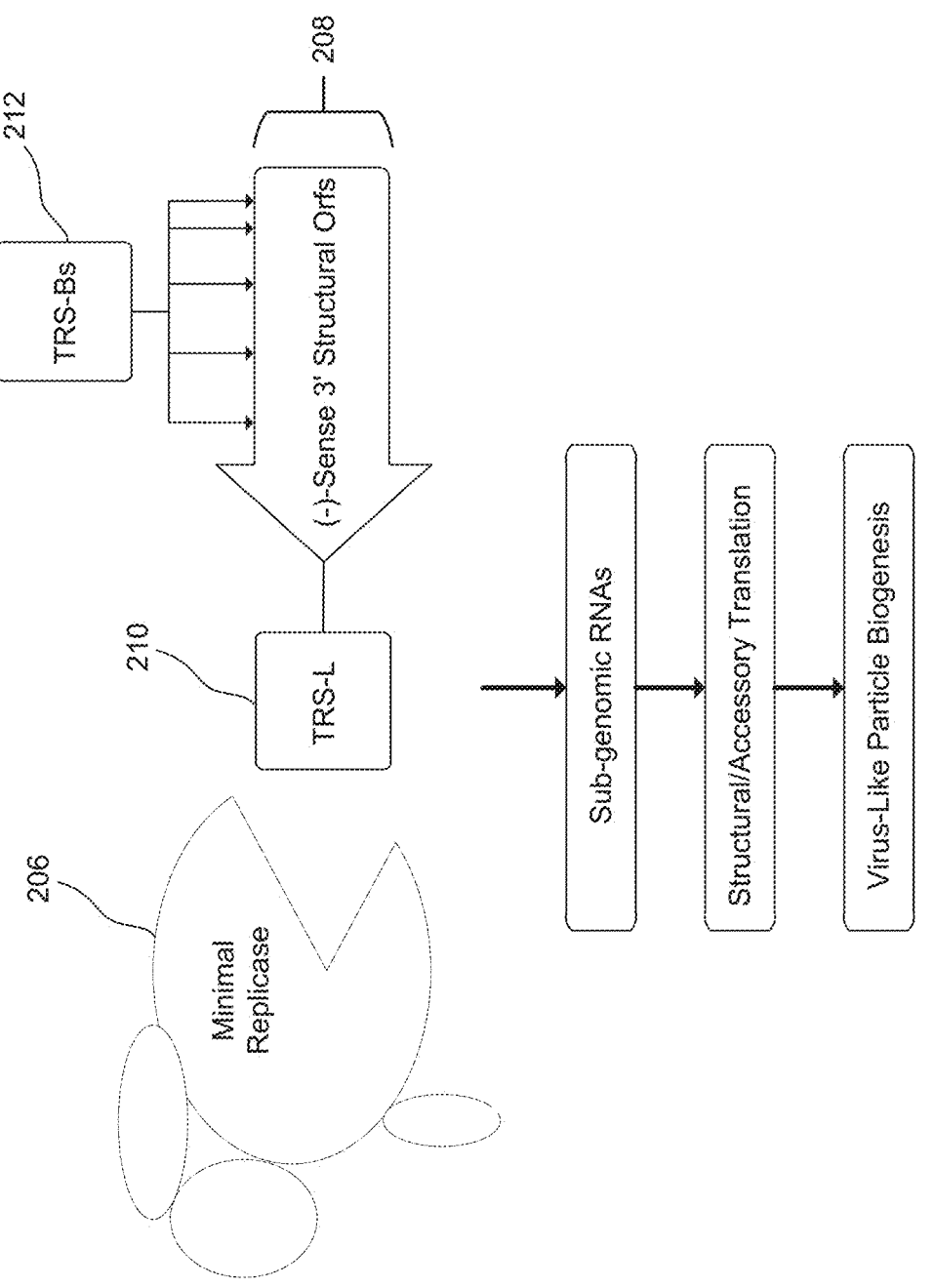

Another aspect of the present disclosure relates to the placement of a viral RNA transcript in a (−) sense orientation, which may prevent the generation of structural components in the absence of a replicase system and enable the efficient promotion of native stoichiometry of the structural components in a viral envelope, such as in FIG. 2A and FIG. 2B.

Another aspect of the present disclosure, e.g., as discussed further herein with reference to FIG. 2A, relates to genetically fusing a 5' untranslated region (5'-UTR) of a SARS-CoV-2 genome, such as the first 500 nucleotides of the SARS-CoV-2 genome, with a transcriptional regulator region, such as a transcriptional regulatory body sequence (TRS-B), of a S protein gene of a pStructural plasmid, which may enable transcriptional generation of transcriptional regulatory sequence leader (TRS-L) sequences for a replicase system.

Another aspect of the present disclosure relates to the generation of a minimal replicase system, pReplicase, capable of driving transcription of messenger RNAs coding for major structural and accessory proteins that constitute the viral envelope as well as intraviral content. The minimal replicase system may include one or more of the following aspects: (i) genetically fusing a SARS-CoV-2 nsp5 gene to a 5' end of a genetic element of a minimal replicase system, which may introduce a SARS-CoV-2 Nsp5 viral protease to a N-terminus of a minimal replicase polypeptide upon translation to potentially enable maturation of replicase components through protease activity and increase the efficiency of replicase generation; (ii) removal of a SARS-CoV-2 nsp11 coding region and proximal ribosomal frameshift sites to potentially yield higher expression of a minimal replicase system through constitutive expression of a minimal replicase polypeptide; and (iii) cloning a minimal replicase system into a low copy plasmid to potentially prevent toxicity to an *E. Coli* microbiological DNA replicator. For example, a minimal replicase system including the above aspects may have a genetic element comprising 5'-nsp5-7-8-9-10-orf1b(nsp12-13-14-15-16)-3', where nsp5, 7, 8, 9, and 10 are part of orf1a, that forms a minimal orf1a-b polypeptide comprising Nterminus-Nsp5-7-8-9-10-12-13-

14-15-16-Cterminus upon translation. In other words, the nsp6 and nsp11 coding regions may be deleted and the remaining portions comprising nsp5-7-8-9-10 and nsp-12-13-14-15-16 (orf1b) may be genetically fused in frame with one another. A two-plasmid system including such a minimal replicase system may provide an increased level of safety in producing VLPs. The method 100 of FIG. 1 may, for example, comprise the generation of such a minimal replicase system as well as the herein mentioned aspects of the present disclosure pertaining to the generation of pStructural and pReplicase.

Another aspect of the present disclosure relates to the optimization of plasmid ratios, such as the ratio of pReplicase to pStructural, for the biased production of plasmid-related components to potentially increase VLP yield from expressing tissue cultures. For example, a plasmid mass ratio of 1:1 for pReplicase to pStructural may be used to potentially maximize VLP yield.

In some embodiments, the optimized genetic system may enable the production of morphologically and biochemically similar VLPs to that of native infectious SARS-CoV-2. These VLPs may have the potential to be novel immunogens for eliciting a broad and protective response to SARS-CoV-2 challenge. However, in other embodiments, it is contemplated that the teachings of the present disclosure may be applied more generally to other virus types (e.g., other coronaviruses, beta-coronaviruses, SARS-CoV-1, and MERS), such as the disposal of a significant portion of the viral genome in the production of non-infectious, replication-incompetent VLPs, without departing from the scope or spirit of the present disclosure. Such teachings of the present disclosure may be used, for example, in the rapid development of similar polyvalent immunogens to newly emerging viruses, which may comprise VLPs with a high-valency structural proteome.

In some embodiments, the optimized genetic system may comprise the transfection of cells, such as Vero cells or Caco-2 cells, with one or more plasmids, such as pStructural and pReplicase, to produce VLPs. An optimized ratio of the one or more plasmids may be used to enable increased efficiency of VLP production in the transfected cells. For example, a higher ratio of pReplicase to pStructural, such as 3:1, may be used. In another example, a 1:1 mass ratio of pReplicase to pStructural may be used. Cells to be transfected may be chosen based on at least one of VLP production ability and ease of transfection. For example, cells may be chosen which have the ability to replicate SARS-CoV-2 during native infection and have the ability to be efficiently transfected with plasmid DNA. Transfection may be conducted using a transfection reagent. For example, a polycationic polymer, such as polyethyleneimine, may aid in the transfection of both Vero cells and Caco-2 cells with the pReplicase and pStructural plasmids. The supernatant surrounding the transfected cells may be harvested and purified for VLPs through purification techniques know in the art. For example, density gradient centrifugation may be used to remove cell debris, serum proteins, and other non-VLP debris.

In some embodiments, VLPs may be coupled to an assay for detection of antibodies from virus-infected individuals. A biological sample containing antibodies from a patient may be introduced to the VLPs on a test strip assay to see if any antibodies bind to the VLPs. For example, patient serum may be flowed over the VLPs, and techniques known in the art may be used, such as in ELISA using anti-human antibodies conjugated to a chemiluminescent protein horse-radish peroxidase, to determine if any antibodies from the patient serum bind to the VLPs.

Referring now to the drawings, FIG. 1 illustrates a flowchart depicting an exemplary method 100 for producing VLPs, such as beta-coronavirus VLPs, which may be replication-incompetent. The method may comprise, in Block 102, generating a modified viral genome based on a viral genome, wherein a portion of the viral genome is removed to generate the modified viral genome configured to yield VLPs that are unable to replicate. For example, the modified viral genome may comprise less than ⅔ of the viral genome, and the removed portion of the viral genome may comprise more than ⅓ of the viral genome. In another example, the viral genome may be a SARS-CoV-2 genome, and the modified viral genome may be a modified SARS-CoV-2 genome. The method may further comprise, in Block 104, producing one or more VLPs using the modified viral genome. For example, the VLPs may be produced using the transfection and harvesting techniques disclosed herein, such as by transfecting one or more cells (e.g., at least one of Vero cells or Caco-2 cells) with the modified viral genome and harvesting the VLPs generated by the cells. The VLPs produced may, for example, be implemented in a variety of antibody detection tests, vaccines, as a standard for detection of virus envelope antigens, or in investigating virus transmission as discussed further herein.

In some embodiments, the generating of Block 102 may comprise generating the modified viral genome, wherein the modified viral genome comprises a first plasmid coding for viral structural and accessory proteins and a second plasmid coding for a minimal replicase system configured to drive transcription of the first plasmid. For example, the first plasmid may be pStructural as described herein, and the second plasmid may be pReplicase as described herein. Such segmentation of the viral genome into a two-plasmid system may enable an increased level of safety in producing VLPs. In another example, the first plasmid may be placed in a (−) sense orientation, which may prevent the generation of the structural and accessory proteins encoded in the first plasmid in the absence of a minimal replicase system, providing a safety mechanism in the VLP production. The first plasmid being placed in a (−) sense orientation may also enable efficient promotion of native stoichiometry (native to the virus) of the structural and accessory proteins in the VLPs, such as demonstrated in FIG. 2A and FIG. 2B. In yet another example, the first plasmid may comprise self-cleaving RNA elements configured for scarless RNA transcription, such as HHr and HDVr. Such self-cleaving RNA elements may enable scarless expression of RNA that mimics the native ends of the viral genome, such as by removing non-viral genetic material upon completion of RNA polymerase II transcription, which may be done in the generation of pStructural of the present disclosure. In yet another example, the second plasmid may be a low copy plasmid, which may potentially prevent toxicity to a microbiological DNA replicator cell (e.g., E. Coli).

In some embodiments, the generating of Block 102 may comprise generating the modified viral genome, wherein the modified viral genome is a SARS-CoV-2 genome and comprises a first plasmid coding for viral structural and accessory proteins, such as pStructural, and a second plasmid coding for a minimal replicase system, such as pReplicase, configured to drive transcription of the first plasmid. Various genetic modifications may be made to the first plasmid as well as second plasmid in the generating of Block 102. For example, a SARS-CoV-2 nsp5 gene may be genetically fused to a 5' end of the second plasmid. Such fusing of a SARS-CoV-2 nsp5 gene may introduce a SARS-CoV-2 Nsp5 viral protease to a N-terminus of the second plasmid upon translation, which may potentially enable maturation of minimal replicase system components through protease activity, such as demonstrated by FIG. 4A, and increase the efficiency of minimal replicase system generation. In another example, at least one of a SARS-CoV-2 nsp6 coding region or a SARS-CoV-2 nsp11 coding region of the SARS-CoV-2 genome may be removed in generating the second plasmid. Removal of the SARS-CoV-2 nsp6 and nsp11 coding regions may enable increased efficiency of the minimal replicase system. In a more specific example, a SARS-CoV-2 nsp11 coding region of the SARS-CoV-2 genome may be removed in generating the second plasmid, and a SARS-CoV-2 nsp10 coding region of the SARS-CoV-2 genome may be genetically fused in-frame with a SARS-CoV-2 nsp12 coding region of the SARS-CoV-2 genome in generating the second plasmid. Such removal of the SARS-CoV-2 nsp11 coding region and in-frame fusing of the SARS-CoV-2 nsp10 and nsp12 coding regions may enable higher expression of downstream polypeptides of the second plasmid, such as a downstream Nsp12-13-14-15-16 polypeptide, which may constitute a portion of the core replicase machinery of the minimal replicase system. Such higher expression of the minimal replicase system may further be aided by removing ribosomal frameshift sites of the SARS-CoV-2 genome proximal to the SARS-CoV-2 nsp11 coding region in generating the second plasmid. In yet another example, a 5'-UTR of the SARS-CoV-2 genome may be genetically fused with a transcriptional regulator region of a S protein gene of the SARS-CoV-2 genome in generating the first plasmid. In a more specific example, the first 500 nucleotides of the SARS-CoV-2 genome comprising a 5'-UTR of the SARS-CoV-2 genome may be genetically fused with a TRS-B of a S protein gene of the SARS-CoV-2 genome in generating the first plasmid. Such fusing of a 5'-UTR with the transcriptional regulator region or TRS-B of the S protein gene may enable transcriptional generation of TRS-L sequences for the minimal replicase system.

The VLPs produced using method 100 may enable safe use of particles that mimic virus structure as well as natively configured envelope antigens and core nucleoprotein in a variety of antibody detection tests, vaccines, as a standard for detection of virus envelope antigens, or in investigating virus transmission. For example, the VLPs may be incorporated into an antibody detection test and may potentially increase the sensitivity of the antibody detection test with a plurality of different envelope antigen types of the VLPs producing a polyclonal response, rather than just testing for a single antibody type. In another example, the VLPs may be incorporated into virus transmission studies, such as into a nebulized liquid that is dispersed in an environment, wherein the VLPs may mimic transmission of the native virus within that environment. Method 100 may also enable modular insertion or deletion of various envelope antigens from the VLPs. For example, the second plasmid may be genetically modified to insert or delete envelope antigen transcripts, such as envelope antigen transcripts of naturally occurring mutations of the virus (e.g., mutations found in SARS-CoV-2 variants of concern). In such a way, a method for producing SARS-CoV-2 VLPs may be adapted using the modular insertion or deletion of envelope antigens into a method for producing other VLP types, such as MERS VLPs or VLPs of different SARS-CoV-2 variants. Similarly, spike-less SARS-CoV-2 VLPs may be produced using method 100 if a S protein coding region is deleted in the second plasmid. Such spike-less SARS-CoV-2 VLPs may enable the detection of non-S protein binding antibodies, such as in an antibody detection test. It is contemplated that other various combinations of envelope antigen types, such as S, M, E, N, or Orf3a SARS-CoV-2 antigens, may be modularly added and removed without departing from the scope or spirit of the present disclosure. For the purposes of this disclosure, envelope antigen types include nucleoproteins (e.g., N) that define, e.g., a structure of, the viral envelope even though they are not integral proteins of the envelope.

It is contemplated that the VLPs of the present disclosure, such as those produced using method 100, may be utilized to generate monoclonal antibodies against viral antigens. For example, VLPs could be administered into an animal model to have said animal generate antibodies against all envelope surface antigens and intraviral content of the VLPs. Animal cells producing the antibodies may then be isolated and confirmed to produce antibodies against viral antigens as is customary in the art. Such antibodies may then be harvested from the animal cells.

In some embodiments, the present disclosure may comprise a composition comprising one or more VLPs, such as beta-coronavirus VLPs, that are morphologically and biochemically similar to a virus and are unable to replicate, wherein the VLPs are associated with a modified viral genome having a genome of the virus with a removed portion. For example, such VLPs may comprise a high-density display of at least one envelope antigen type of the virus in a native stoichiometry encoded by the genome of the virus. Such envelope antigens of the virus may be present in the VLPs in a native configuration as observed in the virus. For example, the morphology and biochemistry of the envelope antigens as well as the location, orientation, and local environment of the envelope antigens may be the same as observed natively in the virus. The at least one envelope antigen type may, for example, be at least one of S, M, E, N, or Orf3a SARS-CoV-2 antigens; however, it is contemplated that any of a variety of virus envelope antigens, such as envelope antigens associated with virus variants or mutations, may be modularly inserted or removed from the VLPs through modification of the viral genome. The VLPs of the composition may be produced, for example, using method 100 and may incorporate the various genetic modifications of method 100 into the modified viral genome associated with the VLPs.

In some embodiments, the virus may be SARS-CoV-2, and the genome of the virus may be a SARS-CoV-2 genome. The modified viral genome may comprise a SARS-CoV-2 nsp5 coding region of the SARS-CoV-2 genome genetically fused with a SARS-CoV-2 nsp7 coding region of the SARS-CoV-2 genome, such as in FIG. 2A. Additionally, a SARS-CoV-2 nsp10 coding region of the SARS-CoV-2 genome may be genetically fused in-frame with a SARS-CoV-2 nsp12 coding region of the SARS-CoV-2 genome with a SARS-CoV-2 nsp11 coding region of the SARS-CoV-2 genome removed. Such modification of the viral genome may enable an increase in efficiency and expression of VLP-producing components, such as the minimal replicase systems disclosed herein (e.g., pReplicase).

In some embodiments, the composition may be a vaccine, such as a SARS-CoV-2 vaccine. For example, the composition may comprise a solution configured to contain the one or more VLPs. Such a composition may be administered to a patient and educate the patient's immune system toward at least one envelope antigen type presented by the VLPs. For example, the VLPs may comprise a plurality of envelope antigen types, such as S, M, E, N, and Orf3a SARS-CoV-2 proteins, and may elicit a broad polyclonal immune response. The VLPs may preserve the native structure and stoichiometry of surface antigens observed in the virus but may be unable to replicate and cause unnecessary inflammatory responses, enabling a safe, robust vaccine.

In some embodiments, the composition may be a standard for detection of one or more envelope antigen types of the virus. For example, the one or more envelope antigen types may comprise at least one of S, M, E, N, or Orf3a SARS-CoV-2 antigens, and the composition may be the standard for comparison in a detection test for the one or more envelope antigen types. In a more specific example, the one or more envelope antigen types may comprise all non-S SARS-CoV-2 antigen types in a native configuration, resulting in spike-less VLPs, and the composition may be a negative control standard for comparison in a detection test for non-S binding antibodies (e.g., M, E, Orf3a, and N antibodies), such as in a detection test for non-S binding antibodies within patient serum. The modularity of the envelope antigens associated with the VLPs of the present disclosure may enable such deletion of particular envelope antigen types of the virus or insertion of additional envelope antigen types through modification of the viral genome, such as modification of the disclosed pStructural.

In some embodiments, the composition may be a nebulized liquid containing the one or more VLPs. For example, the nebulized liquid, such as nebulized water or a nebulized physiological buffer (e.g., phosphate-buffered saline solution), may contain one or more SARS-CoV-2 VLPs. Such a composition may enable the study of various viral transmission routes without the risks associated with native viruses by safely observing the behavior of replication-incompetent VLPs when dispersed into an environment, such as in a nebulized liquid.

In some embodiments, the present disclosure may comprise an antibody detection test comprising one or more VLPs, such as beta-coronavirus VLPs, that are unable to replicate and comprise a plurality of envelope antigens of a virus in a native configuration, such as the VLPs of method 100. The antibody detection test may also comprise a means for exposing the one or more VLPs to one or more antibodies associated with the virus. Such means for exposing may comprise flowing a solution potentially containing the one or more antibodies over the one or more VLPs. For example, the VLPs may be coupled to a surface, such as a surface of a test strip assay, and the solution, such as patient serum, may flow over the surface, exposing the VLPs to the antibodies. In another example, the antibody detection test may comprise a means for detecting any binding of the antibodies to the VLPs after exposure to the antibodies, such as by enzyme-labelling the antibodies or using any of a number of antibody labeling and detection methods known in the art. The antibody detection test may, for example, be an enzyme-linked immunosorbent assay (ELISA).

In some embodiments, the virus may be SARS-CoV-2, and the VLPs may comprise a plurality of S, M, and N SARS-CoV-2 proteins in a native configuration. For example, the antibody detection test may be an antibody detection test for S, M, and N SARS-CoV-2 protein binding antibodies, such as those potentially found in patient serum, and may utilize the S, M, and N SARS-CoV-2 proteins of the VLPs in detecting S, M, and N SARS-CoV-2 protein binding antibodies. It is contemplated that the VLPs may comprise additional envelope antigen types, such as S, M, E, N, or Orf3a SARS-CoV-2 antigens. For example, the VLPs may comprise a plurality of S, M, E, and N SARS-CoV-2 proteins in a native configuration. In another example, the VLPs may comprise all of envelope antigens of native SARS-CoV-2, enabling diagnostic detection of all SARS-CoV-2 antibodies associated with SARS-CoV-2 envelope antigens.

In some embodiments, the virus may be SARS-CoV-2, and the VLPs may be spike-less VLPs comprising a plurality of non-S SARS-CoV-2 envelope antigen types in a native configuration. For example, the plurality of non-S SARS-CoV-2 envelope antigen types may comprise all non-S SARS-CoV-2 antigen types in a native configuration, resulting in spike-less VLPs, and the antibody detection test may be an antibody detection test for non-S binding antibodies (e.g., M, E, Orf3a, and N antibodies), such as in an antibody detection test for non-S binding antibodies within patient serum. The modularity of the envelope antigens associated with the VLPs of the present disclosure may enable such deletion of particular envelope antigen types of the virus or insertion of additional envelope antigen types through modification of the viral genome, such as modification of the disclosed pStructural.

Although many of the following sections are largely directed toward SARS-CoV-2 VLPs, it is contemplated that, in other embodiments, the teachings disclosed herein may be applied more generally to other virus types and associated VLPs without departing from the scope or spirit of the present disclosure.

Roles of Structural and Accessory Factors in SARS-CoV-2 VLP Assembly:

Introduction

Nascent SARS-CoV-2 structural proteins S, E, M, Orf3a, and Orf7b are predicted to co-translationally fold into the endoplasmic reticulum membrane as transmembrane proteins, similar to SARS-CoV-1. These structural proteins are predicted to then coalesce along the secretory pathway, nucleated by the N protein and viral RNA genome. These molecular interactions then form the basis of a viral bud that deforms the membrane of secretory vesicles, ultimately forming a membrane enveloped viral particle residing in the lumen of the vesicle. Newly abscised virus is then predicted to traffic through the Golgi apparatus and be secreted from the infected cell upon vesicular fusion with the plasma membrane. These cellular and molecular events are predicted from more classical models of coronavirus biogenesis, however, it remains unclear if key molecular steps have differentiated in the emergent SARS-CoV-2 species. Furthermore, a deeper mechanistic understanding of SARS-CoV-2 assembly dependencies may help to develop immunogens with better production efficiency, higher safety profiles, and immunological potency.

In order to generate the sub-genomic RNAs that form the basis of message for ribosomal translation of coronavirus proteins, the (+)-sense genomic RNA may be copied into an anti-sense (−) strand. The SARS-CoV-2 genome, like other related coronaviruses, encodes a high-fidelity RNA-dependent RNA polymerase (RDRP) complex that replicates the (+)-sense genome and subsequently generates sub-genomic RNAs through a process of template switching that ultimately encodes the non-structural, structural, and accessory proteins.

To study the biogenesis of SARS-CoV-1, like other high containment (+)-sense RNA viruses, researchers resort to cloning viral genes into DNA and typically drive viral or messenger RNA by strong promoters and synthetic RNA elements. Studies of SARS-CoV-1 and SARS-CoV-2 assembly have relied on co-expression of combinatorial mixtures of cloned structural genes to investigate the role of each viral protein and their subdomains in assembly. This reductive approach, while still powerful for defining the minimal system required to make a VLP, may not produce viral structural components in their native stoichiometric amount, resulting in a high degree of heterogeneity in VLPs. For SARS-CoV-2, recent transcriptomics data demonstrates that each structural transcript is produced in a defined amount relative to other transcripts, due to a transcriptional template switching mechanism used by RDRP complexes. This indicates that each sub-genomic RNA has evolved enhancing or inhibitory elements at template switching junctions in order to modulate RDRP-mediated transcription at specific sites in the genome. This results in a biased stoichiometric production of structural and accessory proteins relative to antiviral and replicase components. The importance of this choreographed template switching is highlighted by studies using altered template switching regions to enhance the safety of and attenuate the virulence of SARS-CoV-1.

Ultimately, approaches for VLP assembly that do not rely on replicase machinery may not reproduce the spatiotemporal production of each viral protein and could result in artifactual assembly events not found in a native infection. Conversely, the production of mutant viruses from synthetic full-length genomic RNA is laborious and challenging due to the large size of the viral genome. Furthermore, this latter approach requires BSL-3 facilities as it results in the production of potentially lethal mutant viruses. A minimal reverse genetics system has the benefits of being manipulatable in BSL-2 facilities, facile for genetic mutation, and capable of producing replication incompetent virion-like structures that can serve as the basis of a vaccine and/or diagnostic detection of antibodies to SARS-CoV-2.

Analysis and Data

In some embodiments, the present disclosure teaches a safe BSL-2 reverse genetics system for SARS-CoV-2. This system may enable facile genetic control to potentially produce SARS-CoV-2 VLPs that maintain antigenic characteristics but are unable to replicate. The system may utilize the removal of $>\frac{1}{3}$ of the genome (portions of orf1a), meeting CDC guidelines and BSL-2 criteria. Further, the genome (orf1b and structural/accessory orfs) may be segmented with no overlap or homology between the remaining ($<\frac{2}{3}$) genome to potentially reduce the risk of recombination events. A portion of orf1a and the entirety of orf1b may be reverse transcribed into cDNA and cloned into an RNA pol II driven mammalian expression vector, referred herein as pReplicase. Additionally, the orfs encoding the structural and accessory factors may be reverse transcribed and cloned into a similar RNA pol II driven mammalian expression vector, referred herein as pStructural. Self-cleaving RNA elements (HHr/HDVr) may be added to the extreme 5'- and 3'-UTR of the pStructural plasmid to enable scar-less (−)/(+)-sense RNA transcription via a SARS-CoV-2 minimal replicase system, pReplicase. The resulting segmented reverse genetics system, such as the reverse genetics system of FIG. 2A, may produce RDRP-mediated sub-genomic RNA transcripts of the structural orfs, such as in FIG. 2B, in transfected cells.

FIGS. 2A and 2B illustrate an exemplary embodiment of a minimal replicase SARS-CoV-2 virus-like particle system. In FIG. 2A, shown is an exemplary segmented reverse genetics system of the minimal replicase SARS-CoV-2 virus-like particle system, wherein a Nsp5 protease and Nsp7-16 (RDRP/RNA metabolism enzymes, Nsp7 to Nsp16) encoding transcript 202 as well as a 3' structural and accessory protein encoding transcript 204, which may be placed in a (−) sense orientation, are shown to be driven by a cytomegalovirus (CMV) immediate early enhancer and promoter (RNA pol II). For example, the Nsp5 protease and Nsp7-16 encoding transcript 202 may comprise a 5'-nsp5-

7-8-9-10-orf1b(nsp12-13-14-15-16)-3' segment, where nsp11 is deleted and nsp5-7-8-9-10 is fused, in-frame, to nsp12-13-14-15-16, as mentioned above. The resulting Nsp5 protease and Nsp7-16 encoding transcript 202 may code for a minimal replicase complex. The 3' structural and accessory protein encoding transcript 204 may include transcripts for at least one of Orfs S, 3a-b, E, M, 6, 7a-b, 8, 9b-c, or N and may include self-cleaving RNA elements, such as HHr and HDVr, which may facilitate the removal of non-viral genetic material upon completion of RNA polymerase II transcription. Additionally, the 3' structural and accessory protein encoding transcript 204 may include a 5' untranslated region (5'-UTR) of the SARS-CoV-2 genome genetically fused with a transcriptional regulator region, such as a TRS-B, of the S protein gene, which may enable transcriptional generation of TRS-L sequences for the minimal replicase complex. For example, the 5'-UTR may be the first 500 nucleotides of the SARS-CoV-2 genome.

In FIG. 2B, shown is an exemplary production of sub-genomic RNA transcripts and viral structural and accessory proteins in a transfected cell expressing the minimal replicase SARS-CoV-2 virus-like particle system. Upon translation of a minimal replicase complex 206 and maturation of the 3' structural and accessory protein encoding transcript 204 into a mature 3' structural and accessory protein encoding transcript 208, the minimal replicase complex 206 may generate sub-genomic RNAs using transcriptional regulatory sequence leader 210 and transcriptional regulatory body segments 212 (TRS-L/-B) of the mature 3' structural and accessory protein encoding transcript 208 to switch template sites and produce sub-genomic RNA transcripts, which may be translated to generate corresponding viral structural and accessory proteins in a transfected cell. Such protein generation may be in stoichiometric amounts matching the native stoichiometry of SARS-CoV-2 proteins, and ultimately result in virus-like particle biogenesis within the transfected cell. Consequently, the introduction of such a SARS-CoV-2 plasmid system of the present disclosure may result in the production and shedding of virus-like particles, such as the VLPs of FIG. 3.

Figure 2C:
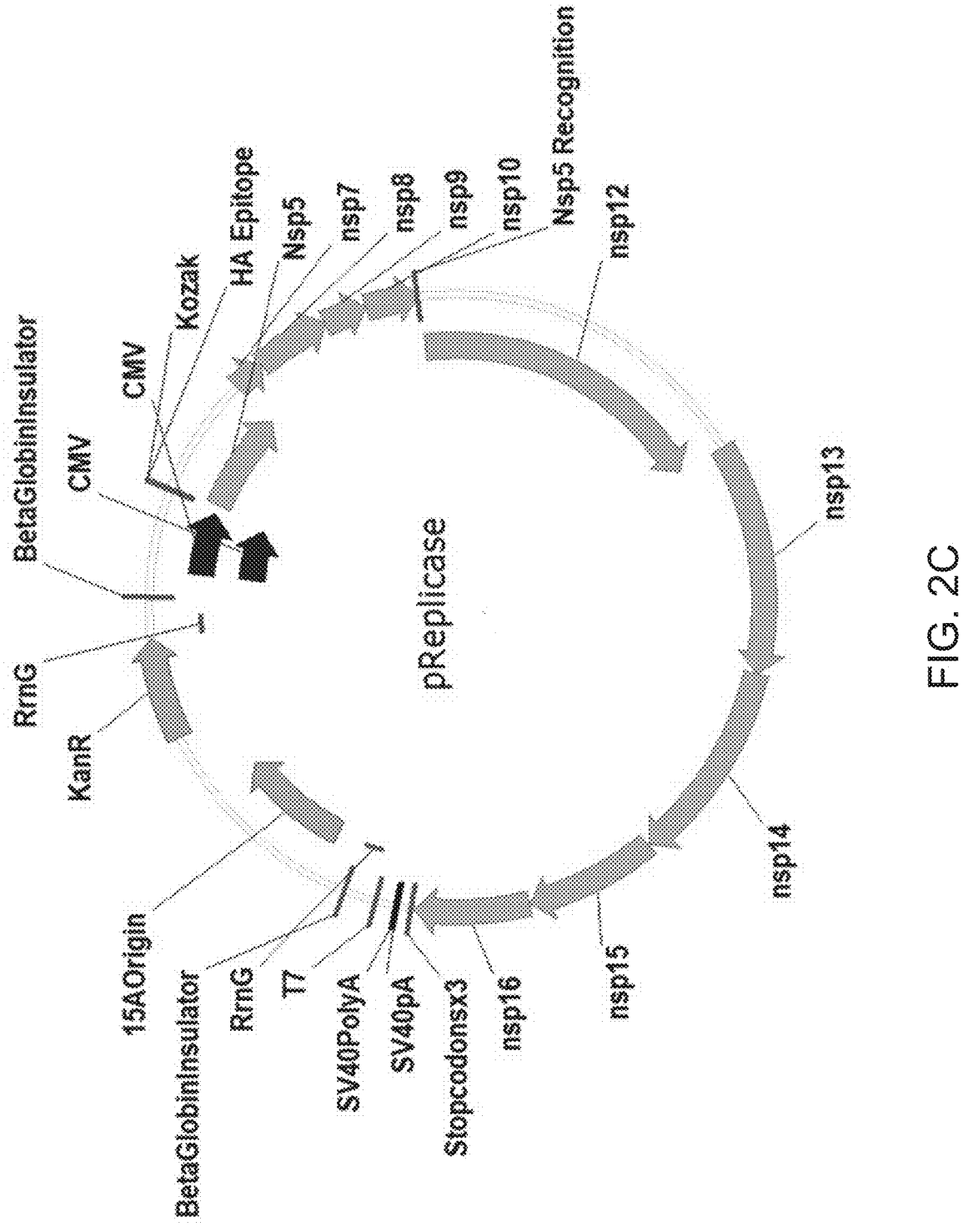
Figure 2D:
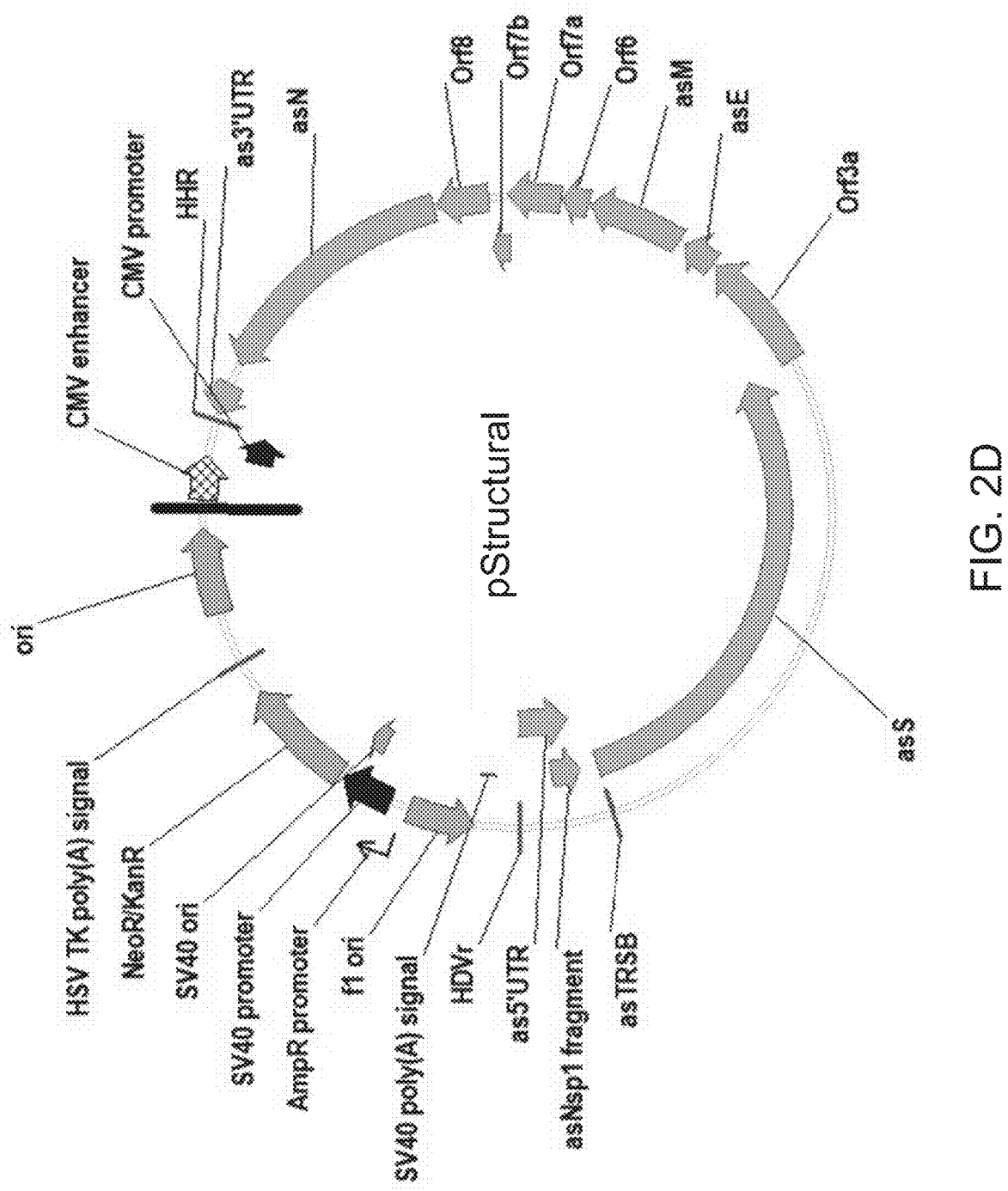

FIGS. 2C and 2D illustrate an exemplary embodiment of a two-plasmid minimal replicase SARS-CoV-2 virus-like particle system, which may comprise the protein encoding transcripts of the segmented reverse genetics system of FIG. 2A. Specifically, FIG. 2C shows an exemplary pReplicase plasmid, such as the pReplicase described further herein, that may comprise the Nsp5 protease and Nsp7-16 encoding transcript 202 of FIG. 2A, and FIG. 2D shows an exemplary pStructural plasmid, such as the pStructural described further herein, that may comprise the 3' structural and accessory protein encoding transcript 204 of FIG. 2A. Such pReplicase and pStructural plasmids may be implemented, for example, in method 100 of FIG. 1 as the first plasmid coding for viral structural and accessory proteins and the second plasmid coding for a minimal replicase system configured to drive transcription of the first plasmid.

Figure 3:
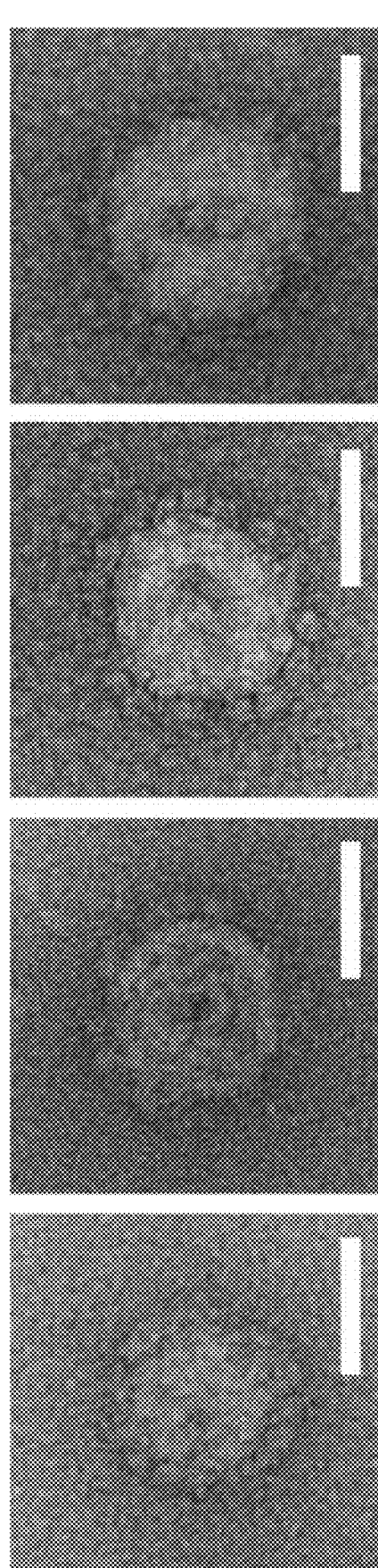
FIG. 3 illustrates a series of exemplary transmission electron microscopy images depicting SARS-CoV-2 virus-like particles produced using an exemplary embodiment of a minimal replicase SARS-CoV-2 virus-like particle system in accordance with one or more embodiments described herein.

FIG. 3 illustrates a series of transmission electron microscopy images depicting SARS-CoV-2 virus-like particles generated using an exemplary embodiment of a minimal replicase SARS-CoV-2 virus-like particle system. The negative stain transmission electron microscopy images shown, with 50 nm scale bars, are of purified VLPs produced by Vero cells. The high-density corona of envelope spike glycoproteins on the surface of VLPs, morphologically similar to infectious SARS-CoV-2, suggests that these VLPs may arise from ordered assembly of structural proteins. Additional structural components such as N, M, and E proteins may cooperate to cluster S protein trimers to promote particle biogenesis. The VLPs produced using a minimal replicase system of the present disclosure may be slightly smaller in diameter than native SARS-CoV-2 particles suggesting an absence of the full RNA genome.

FIGS. 4A-D illustrate a biochemical analysis of an exemplary embodiment of a minimal replicase SARS-CoV-2 virus-like particle system, including cellular mRNA RT-PCR results and western blotting data of purified particles.

Figure 4A:
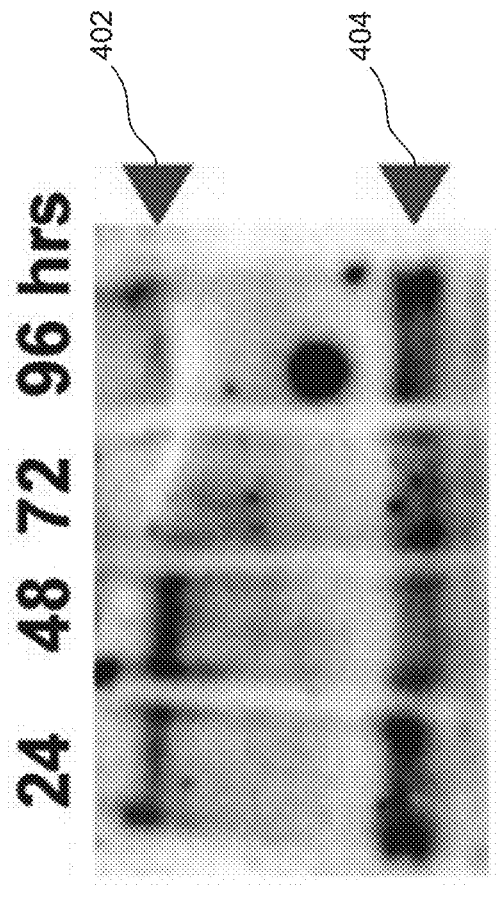

In FIG. 4A, shown is an exemplary western blot time-course analysis of a minimal replicase polypeptide, or transcript, (HA-Nsp5-7-8-9-10-12-13-14-15-16) proteolytic processing by Nsp5 using Hemagglutinin (HA) epitope tagging of the minimal replicase polypeptide (anti-HA western blot), which suggests that Nsp5-mediated processing of the minimal replicase polypeptide occurs due to the lack of unprocessed minimal replicase polypeptide 402 at both 72 hours and 96 hours as well as the presence of processed minimal replicase polypeptide 404 at 24, 48, 72, and 96 hours.

Figure 4B:
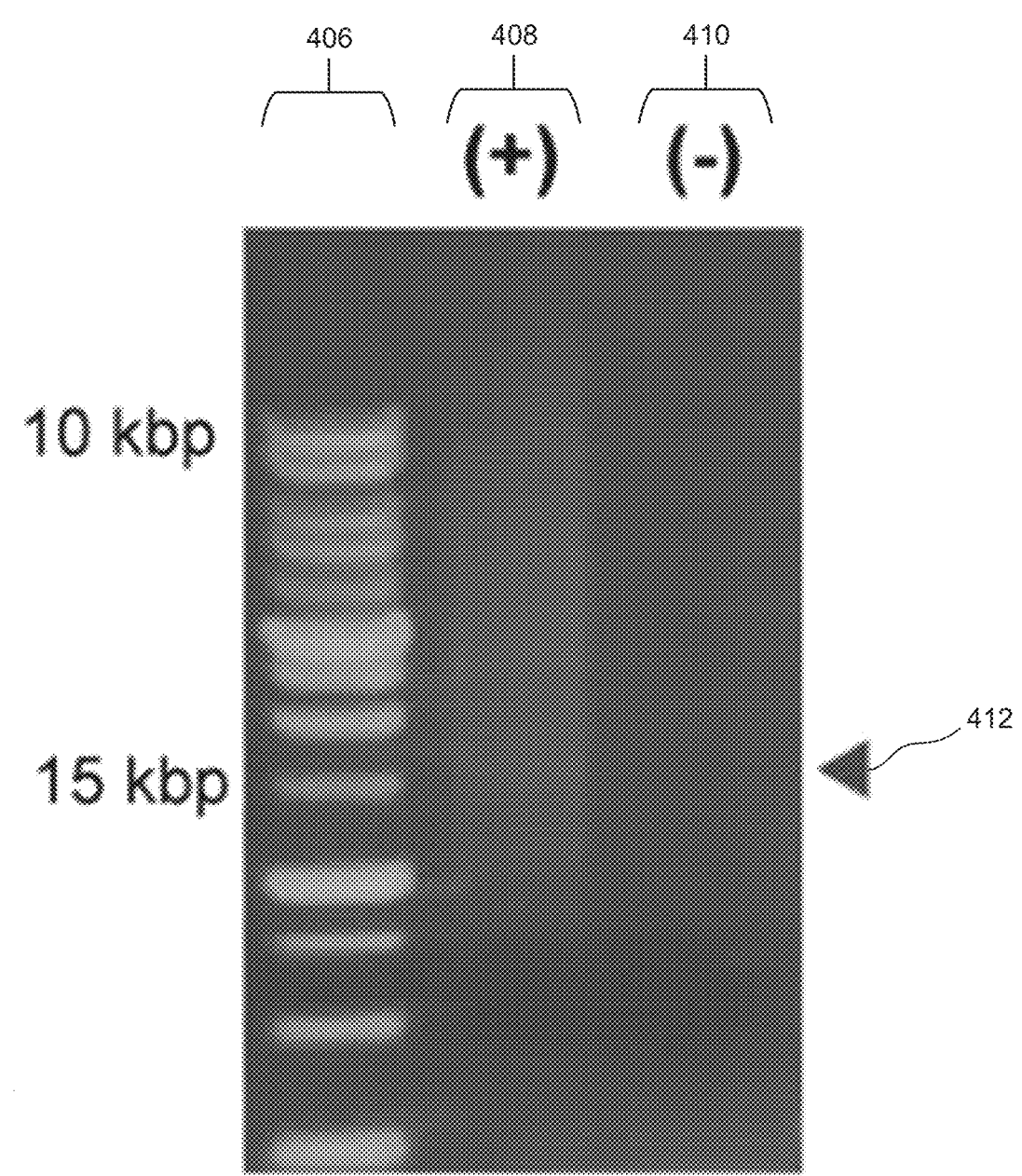

In FIG. 4B, shown are exemplary results of a RT-PCR amplification of SARS-CoV-2 sub-genomic RNA from purified poly-A containing message from cells transfected with a minimal replicase SARS-CoV-2 reverse genetics system of the present disclosure, in lane (+) 408, or mock transfected, in lane (−) 410, using primers specific for the 5' and 3'-UTR of SARS-CoV-2. A ladder reference is included in lane 406. Arrow 412 indicates expected length of the N sub-genomic RNA. The FIG. 4B results suggest that several sub-genomic RDRP products are synthesized in transfected cells given the smear in the (+) lane 408.

Figures 4C, 4D:
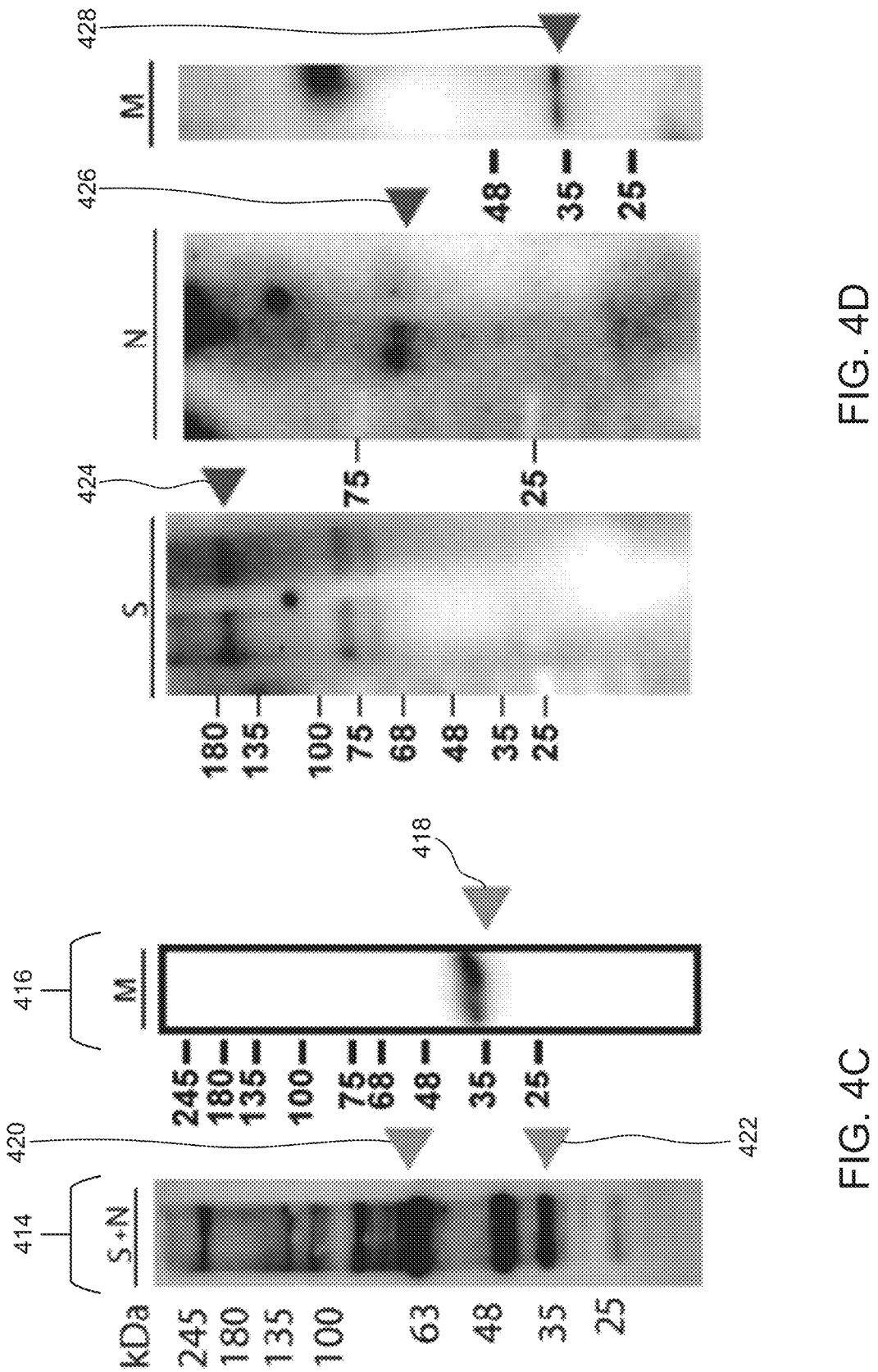

In FIG. 4C, shown is an exemplary anti-N and anti-S western blot 414 as well as an exemplary anti-M western blot 416, both of a cell lysate of Vero cells transfected with a SARS-CoV-2 reverse genetics system of the present disclosure. Arrow 418 demarks a reactive band using anti-M antibody showing a slightly elevated molecular weight of M protein (expected ~25 kDa). Additionally, extensive post-translational modification of both S protein, arrow 420, and N protein, arrow 422, is observed. The FIG. 4C results suggest that the structural proteins S, M, and N are translated in the transfected Vero cells.

In FIG. 4D, shown are exemplary anti-S, anti-N, and anti-M western blots of exemplary SARS-CoV-2 virus-like particles of the present disclosure produced from the transfected Vero cells of FIG. 4C. High and low loading lanes (left and right lanes respectively) are included for both the anti-S and anti-N western blots. The western blots show that mature glycosylated S protein, arrow 424, (expected ~180 kDa) and modified N protein, arrow 426, (~60 kDa) are preferentially incorporated in SARS-CoV-2 VLPs. M protein, arrow 428, is detected in SARS-CoV-2 VLP fractions at a similar molecular weight compared to the M protein in the cell lysate of FIG. 4C, demarked by arrow 418. The FIG. 4D results suggest that the structural proteins S, M, and N may form the basis of released SARS-CoV-2 VLPs. S, M, and N protein genes flank other structural components and accessory factors yet are readily detected in SARS-CoV-2 VLPs, suggesting that additional sub-genomic RNAs may be synthesized and proteins may be produced using the reverse genetics systems and associated minimal replicase systems of the present disclosure.

The reverse genetics systems of the present disclosure may be implemented in a variety of studies, such as studies aimed at understanding the important determinants of structural and accessory factors during SARS-CoV-2 assembly. Such reverse genetics systems may be capable of recapitulating virus assembly using virally produced RDRP-mediated sub-genomic RNAs and thus may preserve the balanced biosynthetic levels of viral proteins that drive SARS-CoV-2 particle production. Such reverse genetics systems may enable defined studies interrogating critical cellular and molecular steps in SARS-CoV-2 biogenesis, thus furthering fundamental viral knowledge and enabling the design of novel immunogens to this deadly pathogen.

As used herein, the recitation of "at least one of A, B or C" is intended to mean "either A, B, C or any combination of A, B and C." The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. A method for producing replication-incompetent coronavirus-like particles, the method comprising:

cloning one-third or less of a coronavirus genome into deoxyribonucleic acid (DNA) forms comprising a first plasmid and a second plasmid, the first plasmid, in a (−) sense orientation, coding for viral structural and accessory proteins, and the second plasmid coding for a minimal replicase system;

introducing the plasmids into cultured cells;

transcribing the first plasmid to produce a structural transcript and transcribing the second plasmid to produce a replicase-encoding transcript;

producing sub-genomic ribonucleic acids (RNAs) with the minimal replicase system from the first plasmid to express S, E, M, and N proteins in native-like stoichiometry; and assembling and releasing virus-like particles using the sub-genomic RNAs and translated products.

2. The method of claim 1, wherein the introducing comprises:

transfecting the cultured cells with the plasmids.

3. The method of claim 2, wherein the transfecting comprises:

transfecting at least one of Vero cells or Caco-2 cells.

4. The method of claim 1, wherein the coronavirus genome is a SARS-COV-2 genome.

5. The method of claim 4, wherein the first plasmid comprises self-cleaving RNA elements configured for scarless RNA transcription.

6. The method of claim 4, comprising genetically fusing a SARS-COV-2 nsp5 gene to a 5' end of the second plasmid.

7. The method of claim 4, wherein at least one of a SARS-COV-2 nsp6 coding region or a SARS-COV-2 nsp11 coding region of the SARS-COV-2 genome is removed when cloning the coronavirus genome to form the second plasmid.

8. The method of claim 4, wherein the cloning comprises:

removing a SARS-COV-2 nsp11 coding region of the SARS-COV-2 genome when forming the second plasmid; and genetically fusing a SARS-COV-2 nsp10 coding region of the SARS-COV-2 genome in-frame with a SARS-COV-2 nsp12 coding region of the SARS-COV-2 genome when forming the second plasmid.

9. The method of claim 4,
wherein the second plasmid is a low copy plasmid.

* * * * *